(12) United States Patent
Shirley et al.

(10) Patent No.: US 9,750,506 B2
(45) Date of Patent: Sep. 5, 2017

(54) OCCLUDING DEVICE FOR OCCLUSION OF A BODY VESSEL AND METHOD FOR MAKING THE SAME

(71) Applicant: Cook Medical Technologies LLC, Bloomington, IN (US)

(72) Inventors: Gary Bradford Shirley, Bloomington, IN (US); Sanket Nayanbhai Patel, Pineville, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 16 days.

(21) Appl. No.: 14/503,864

(22) Filed: Oct. 1, 2014

(65) Prior Publication Data

US 2015/0017317 A1 Jan. 15, 2015

Related U.S. Application Data

(62) Division of application No. 12/165,754, filed on Jul. 1, 2008, now Pat. No. 8,876,852.

(51) Int. Cl.
*A61B 17/12* (2006.01)
*A61B 17/00* (2006.01)
*A61B 50/30* (2016.01)

(52) U.S. Cl.
CPC .... *A61B 17/1215* (2013.01); *A61B 17/12022* (2013.01); *A61B 17/12145* (2013.01); *A61B 50/30* (2016.02); *A61B 2017/00526* (2013.01); *A61B 2017/1205* (2013.01)

(58) Field of Classification Search
CPC ................................................. A61B 17/12022
USPC .......................... 606/200, 157; 424/422, 551
See application file for complete search history.

(56) References Cited

U.S. PATENT DOCUMENTS

| | | | |
|---|---|---|---|
| 4,494,531 A | 1/1985 | Gianturco | |
| 5,074,840 A | 12/1991 | Yoon | |
| 5,133,731 A | 7/1992 | Butler et al. | |
| 5,167,624 A | 12/1992 | Butler et al. | |
| 5,312,415 A * | 5/1994 | Palermo | A61B 17/12022 606/108 |
| 5,439,457 A | 8/1995 | Yoon | |
| 6,280,457 B1 | 8/2001 | Wallace et al. | |
| 7,416,757 B2 * | 8/2008 | Davis, III | A61L 27/34 427/171 |
| 7,857,825 B2 * | 12/2010 | Moran | A61B 17/12022 424/551 |
| 8,057,495 B2 * | 11/2011 | Pal | A61B 17/12022 606/157 |
| 8,101,197 B2 * | 1/2012 | Buiser | A61B 17/12022 424/422 |
| 2005/0261727 A1 | 11/2005 | Davis, III et al. | |

(Continued)

*Primary Examiner* — Vy Bui
(74) *Attorney, Agent, or Firm* — Brinks Gilson & Lione

(57) ABSTRACT

In at least one embodiment of the present invention, a method for making an occluding device for occlusion of fluid flow through a lumen of a body vessel is provided. The method comprises attaching a coating to an embolization coil that is substantially straight. The coating is nominally strained on the substantially straight embolization coil. The embolization coil has a pre-curled tension to facilitate the embolization coil being curled within the lumen of the body vessel when deployed. The embolization coil is restrained from curling until deploying to reduce pre-deployment straining of the coating.

7 Claims, 4 Drawing Sheets

(56) References Cited

U.S. PATENT DOCUMENTS

2007/0005102 A1 1/2007 Keating et al.
2009/0270978 A1 10/2009 Virkler et al.

* cited by examiner

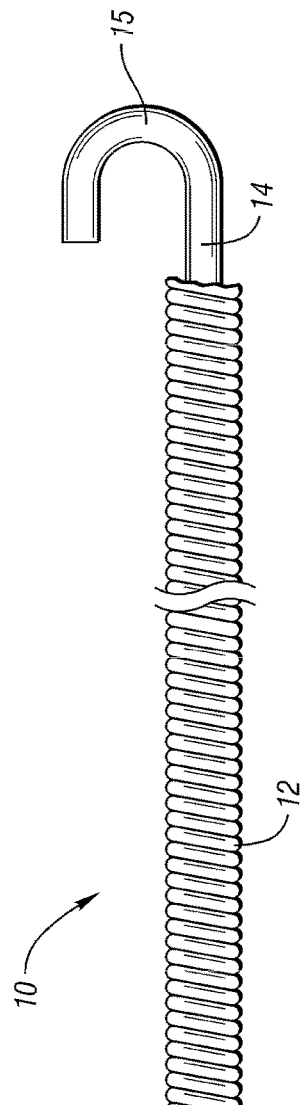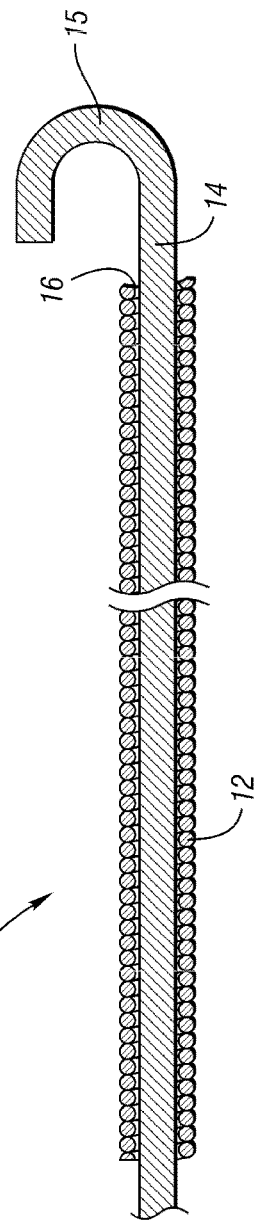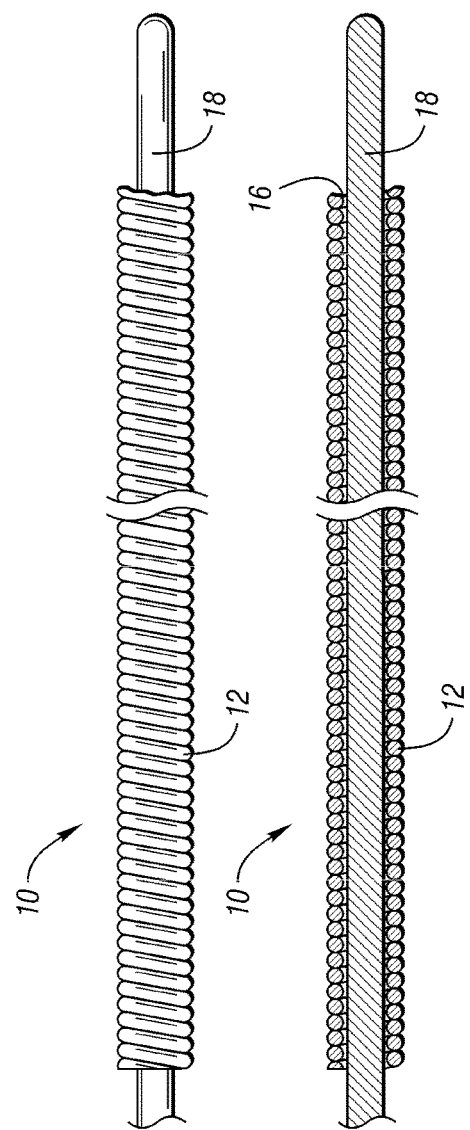
Fig. 1a  Fig. 1b  Fig. 2a  Fig. 2b

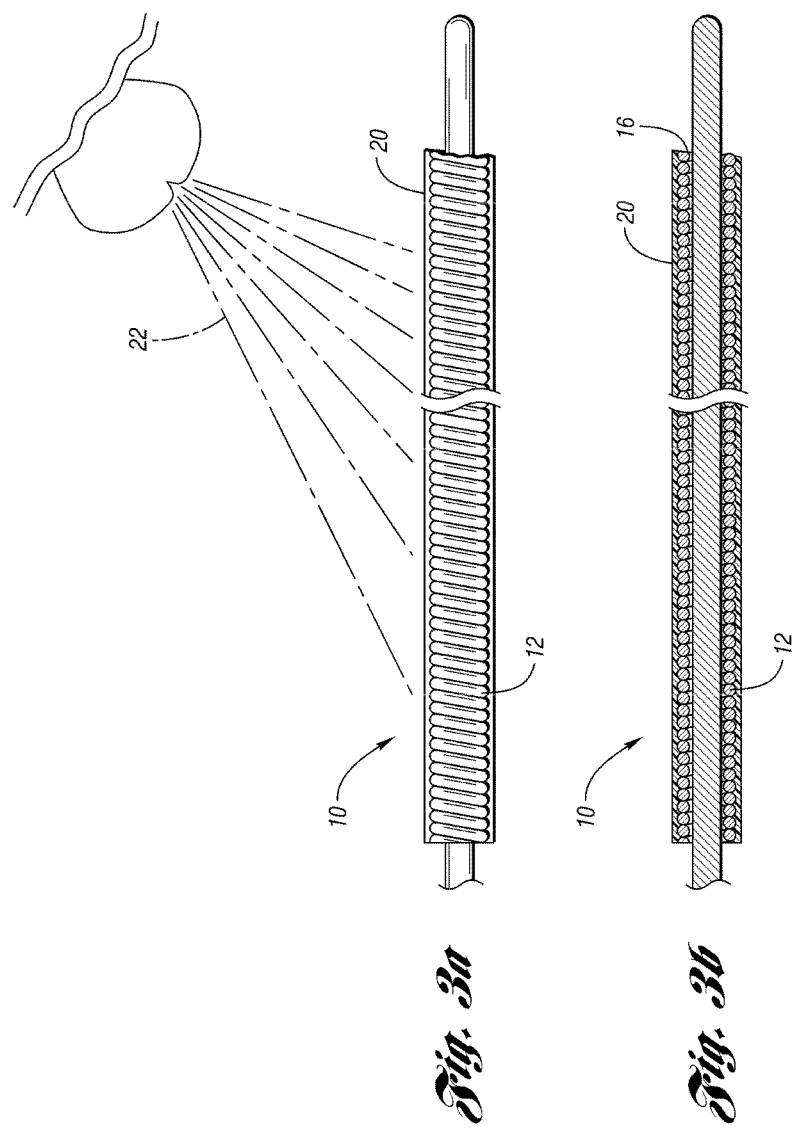

OCCLUDING DEVICE FOR OCCLUSION OF A BODY VESSEL AND METHOD FOR MAKING THE SAME

CROSS-REFERENCE TO RELATED APPLICATIONS

This application is a Divisional of U.S. application Ser. No. 12/165,754, filed on Jul. 1, 2008, entitled "OCCLUDING DEVICE FOR OCCLUSION OF A BODY VESSEL AND METHOD FOR MAKING THE SAME," the entire contents of which are incorporated herein by reference.

BACKGROUND

Field of the Invention

The present invention relates to medical devices. More particularly, the invention relates to occluding devices for occlusion of fluid flow through a body vessel and a method for making the occluding devices.

Background of the Invention

Embolization coils have been used as a primary occluding device for treatment of various arteriovenous malformations (AVM) and varicoceles, as well as for many other arteriovenous abnormalities in the body. Occluding devices are also used to repair abnormal shunts between arteries and veins, prevent or reduce blood flow to tumors, stop hemorrhaging as a result of trauma, and stabilize aneurysms to prevent rupture. Embolization coils may be configured in a variety of sizes with varying diameters and may be made of several different materials including stainless steel and platinum. Moreover, many embolization coils are designed with high tension or stiffness, e.g., between about 60 to 100 weight grams, which may provide the coil with a shape memory. This tension is sometimes referred to as a pre-curled tension. Such coils tend to reform or recanalize back to a coiled or curled shape including, such as for example, a helical and/or looping configuration because of the high tension. Reforming of the coil in the body vessel may be desirable to enhance occlusion of fluid flow therethrough.

Some of these embolization coils may also be coated for various reasons including inducing more robust and stable occlusions and/or improving long term recanalization rates. For example, embolization coils may be coated with a bioresorbable coating, a biocompatible material or another suitable material depending on the desired function.

Current manufacturing processes for coating embolization coils typically involve coating the embolization coil which has a pre-curled tension. The coil is either coated in a curled configuration or allowed to curl after being coating but prior to being deployed. The coated coil is then substantially straightened so as to be advanced through a catheter or other delivery device for introduction into the body vessel. However, some coatings, due to their limited mechanical properties (e.g. stress-strain characteristics), are susceptible to cracking and/or chipping when the coated coil is straightened from its curled shaped. Cracking and/or chipping of the coating, especially prior to introduction of the embolization coil into the body vessel, may result in a loss of the coating and a corresponding loss in occluding performance.

In view of the above, it is apparent that there exists a need for an improved occluding device and a method for making such an occluding device.

SUMMARY OF THE INVENTION

In at least one embodiment of the present invention, a method for making an occluding device for occlusion of fluid flow through a lumen of a body vessel is provided. The method comprises attaching a coating to an embolization coil that is substantially straight. The coating is nominally strained thereon. In order to facilitate the embolization coil being curled within the lumen of the body vessel when deployed, the embolization coil has a pre-curled tension. The embolization coil is restrained from curling until deploying to reduce pre-deployment straining of the coating.

In at least one other embodiment of the present invention, an occluding device for occlusion of fluid flow through a lumen of a body vessel is provided. The device comprises an embolization coil having a pre-curled tension to facilitate the embolization coil being curled within the lumen of the body vessel when deployed. Attached to the embolization coil is a coating. The coating is nominally strained when the embolization coil is substantially straight. The embolization coil is restrained from curling until deploying to reduce pre-deployment straining of the coating.

In at least one other embodiment of the present invention, an embolization kit for occluding fluid flow through a body vessel is provided. The kit comprises an occluding device as described in the foregoing paragraph. The kit further comprises a guide catheter. A microcatheter is configured to be passed through the guide catheter to position the microcatheter in the body vessel and to deploy the occluding device.

Further objects, features, and advantages of the invention will become apparent from consideration of the following description and the appended claims when taken in connection with the accompanied drawings.

BRIEF DESCRIPTION OF THE DRAWINGS

FIG. 1a is a side view of an occluding device in accordance with an embodiment of the present invention;

FIG. 1b is a cross sectional view of the occluding device as depicted in FIG. 1a;

FIG. 2a is a side view of an occluding device in accordance with another embodiment of the present invention;

FIG. 2b is a cross sectional view of the occluding device as depicted in FIG. 2a;

FIG. 3a is a side view of an occluding device in accordance with another embodiment of the present invention;

FIG. 3b is a cross sectional view of the occluding device as depicted in FIG. 3a;

FIG. 4a is an exploded view of an embolization kit in accordance with an embodiment of the present invention;

FIG. 4b is a side view of the embolization kit depicted in FIG. 4a;

DETAILED DESCRIPTION OF THE INVENTION

Figures 4A, 4B:
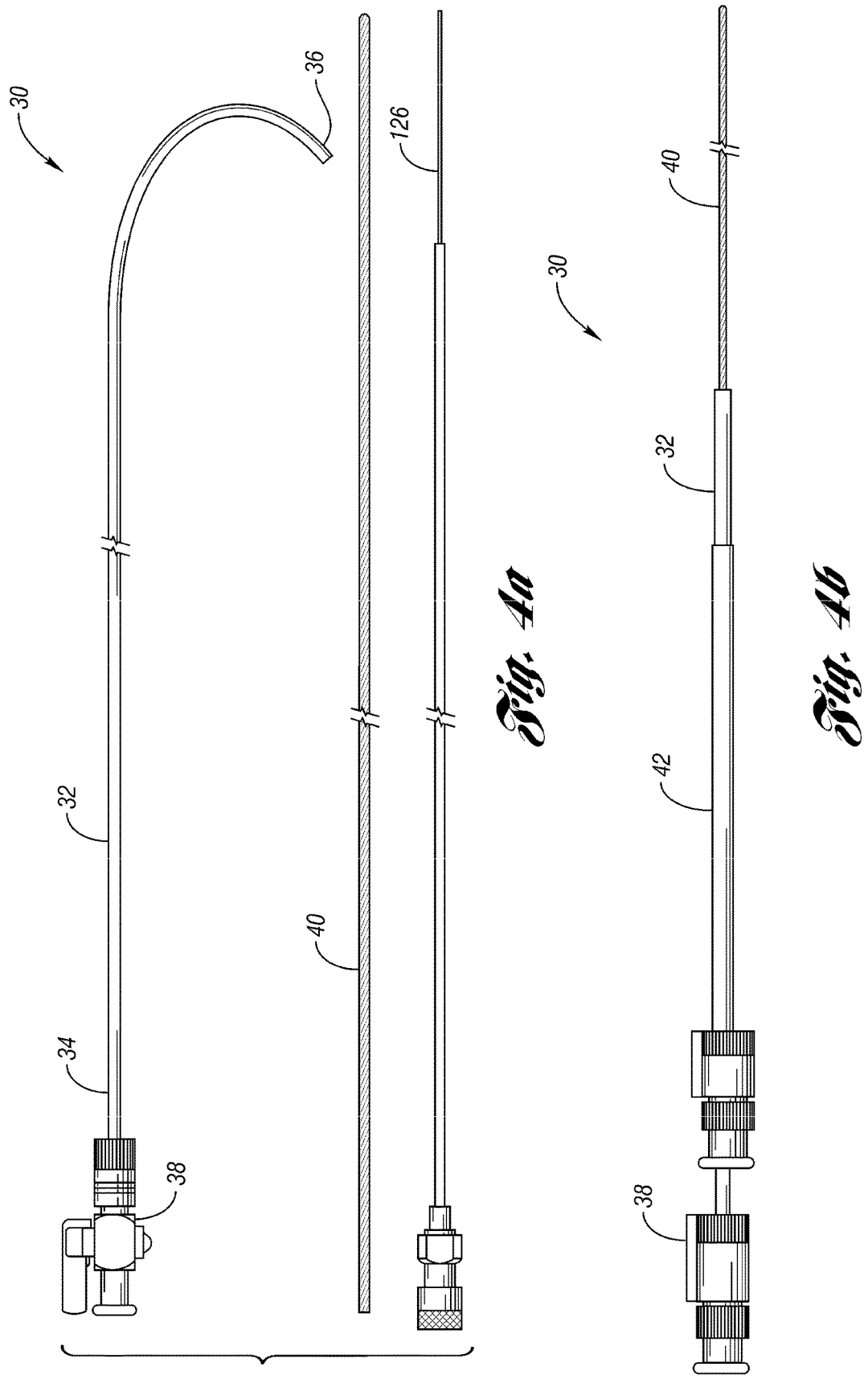

Detailed embodiments of the present invention are disclosed herein. It is understood however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis with the claims and for teaching one skilled in the art to practice the present invention.

Examples of the present invention seek to overcome some of the concerns associated with occluding fluid flow through a body vessel with a coated occluding device while minimizing coating loss from the device, especially until deployment of the device into the body vessel.

Employing the principles of the present invention is, for example, an occluding device for occluding fluid flow through a body vessel, an embolization kit and a method for making the occluding device. The occluding device, which is utilized in the embolization kit, includes an embolization coil that has a pre-curled tension to facilitate the embolization coil being curled. (Note—an "embolization coil" is understood to be a coil for introduction into a body vessel to reduce fluid flow therethrough and will hereinafter be referred to as "coil"). The coil has a coating that was attached thereon when the coil was substantially straight. By attaching the coating to the substantially straight coil, the coating is nominally or negligible stressed when the coil is substantially straight and the coating becomes increasingly stressed when the coil curls. Since the strain (e.g. percent elongation) of a material is related to its stress level (e.g. force per unit area) by the material's modulus (e.g. stress/strain), the coil is also nominally strained when the coil is substantially straight. Nominally strained hereinafter is understood to mean negligibly, insignificantly and/or minimally elongated. For example, a coating applied to substrate that is arranged in a first configuration is negligibly or minimally elongated when the substrate is arranged in the first configuration. This is because the coating is not being significantly stretched or compressed by the substrate and therefore, the coating has a percent elongation near zero. However, if the substrate is flexed or deformed to be arranged in a second configuration, the coating is forced to stretch and/or compress with the substrate and thus, will have corresponding positive and/or negative percent elongation values which deviate from those percent elongation values that are near zero. Accordingly, the coating is no longer nominally strained. Typical methods for measuring strain levels and percent elongation may be used, such as for example, using various "stress coatings" in combination with microscopy to determine the corresponding microstrain values of the coating.

Furthermore, the coil is restrained from curling until deploying in order to minimize or reduce stressing and straining of the coating. The coating, like many materials, cracks and/or chips when it is stressed to strain beyond its ultimate elongation. Accordingly, by minimizing or reducing straining of the coating, cracking and/or chipping of the coating is minimized or reduced, thereby minimizing or reducing coating loss from the coil. Upon deployment, the coil may be positioned at a designated location in the body vessel and freed to curl such that the coating may interact with the inside walls of the body vessel to occlude the body vessel.

Referring now to the drawings, FIGS. 1a and 1b illustrate an embodiment for imparting a curled shape memory to an occluding device 10. A coil 12 of the occluding device 10 has a lumen 16 formed therethrough. The coil 12 may be made by any apparatus known in the art. For example, the coil 12 may be made by any commercial coil winding machine such as a roller deflecting apparatus, a mandrel apparatus, or any other suitable means.

A stylet wire 14 with a curled end 15 may be pulled or advanced through the lumen 16 such that the coil 12 is advanced around the curled end 15. The curled end 15 plastically strains the advancing coil 12 by straining (e.g. tension and/or compression) the coil 12 beyond its yield point. The plastically deformed coil 12 has a pre-curled tension or curled shape memory, which facilitates or causes the coil 12 to curl unless the coil 12 is restrained from curling. Other suitable methods known in the art for imparting a curled shaped memory to the coil 12 may also be used.

Referring now to FIGS. 2a and 2b, a second stylet wire 18 may be advanced through the lumen 16 of the pre-curled tensioned coil 12. The second stylet wire 18 is substantially straight. Substantially straight is hereinafter understood to exclude curled shapes, that is, having coiled and/or looping configurations, but may include some non-linear configurations that are not coiled or looped, which still allow the coil 12 to be loaded into a delivery device, such as a microcatheter, without further straightening of the coil's 12 non-linear configuration. The second stylet wire 18 straightens the coil 12, if the coil 12 has been allowed to curl, and/or restrains the coil 12 from curling. With the stylet wire 18 disposed through the lumen 16, the coil 12 is also substantially straight. Notably, Applicant has discovered that straightening the coil 12 from a curled configuration in this manner does not significantly diminish the curled shape memory of the coil 12.

Figure 6:
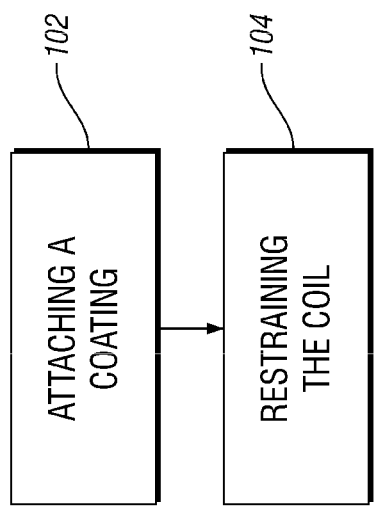
FIG. 6 is a method for making the occluding device in accordance with an embodiment the present invention.

Referring now to FIGS. 3a, 3b and 6, a coating 20 is attached 102 to the coil 12 while the coil is being restrained substantially straight via the second stylet wire 18. The coating 12 may be attached to the coil 12 by applying a coating precursor 22 by any suitably known process, such as for example, spraying, vapor deposition, plating, brush applying, dipping, casting, or affixing. Moreover, the coating precursor 22 may be dried, cured, polymerized and/or coalesced, for example, to form the coating 20. The coating 20 may be used to induce more robust and stable occlusions and/or improve long term recanalization rates. The coating 20 may comprise one or more of the following: extracellular matrix (ECM), such as small intestinal submucosa (SIS), synthetic polyester, such as DACRON™, nylon, rayon, polyester, PTFE, polyurethane, and bioremoldable material.

As known, ECM is a complex structural entity surrounding and supporting cells found within tissues. More specifically, ECM includes structural proteins (for example, collagen and elastin), specialized proteins (for example, fibrillin, fibronectin, and laminin), and proteoglycans, a protein core to which are attached long chains of repeating disaccharide units termed glycosaminoglycans.

In one embodiment, the ECM is comprised of SIS. SIS is a resorbable, acellular, naturally occurring tissue matrix composed of extracellular matrix (ECM) proteins in various growth factors. SIS is derived from the porcine jejunum and functions as a remolding bioscaffold for tissue repair. SIS has characteristics of an ideal tissue engineered biomaterial and can act as a bioscaffold for remolding of many body tissues including skin, body wall, musculoskeletal structure, urinary bladder, and also supports new blood vessel growth. SIS may be used to induce site-specific connective tissue structures, which have been shown to completely replace the SIS material in time.

In another embodiment, the precursor 22 of the coating 20 is small intestinal submucosa gel (SIS gel) including SIS, water, other additives and digestive chemicals. The SIS gel may be applied to the coil 12 and dried to form the coating 20. In one example, the SIS gel is dried by being exposed to a temperature of at least about 30 degrees Celsius (C.), and preferably to a temperature of at least about 37 C. In is understood that certain commercial ovens can control an oven temperature to within +/−2 C, and accordingly, the term "about" refers to the temperature control capabilities of these types of commercial oven.

In a "dry condition," the coating 20 may be brittle. However, the coating 20 may become more flexible when contacted with a water-based fluid, such as for example, body fluids within a body vessel. In one embodiment, the coil 12 is restrained 104 from curling, via the stylet wire 18 or otherwise, until deploying to reduce straining of the coating 20 prior to and until deploying, hereinafter referred to as pre-deployment straining of the coating 20. Preferably, reducing pre-deployment straining of the coating 20 eliminates, minimizes or reduces cracking and/or chipping of the coating 20 prior to deployment of the occluding device 10 into the body vessel. Upon deployment, the coating 20 is exposed to the body fluids which may soften and/or increase flexibility (e.g. increase the ultimate elongation) of the coating 20 such that curling of the coil 12 does not crack and/or chip the coating 20.

In one embodiment, the coating 20 includes SIS. The SIS may adhere to the walls of the body vessel and promote body tissue growth. SIS has a natural adherence to connective cells comprising the connective tissue of the walls of a body vessel. If the device 10 is intended to permanently occlude the body vessel, the device 10 is positioned such that the host cells of the wall will adhere to the SIS and subsequently differentiate, growing into the SIS and eventually occluding the body vessel with the tissue of the walls to which the device 10 was originally adhered. This feature enhances permanent occlusion of the body vessel.

In another particular embodiment, the coating 20 containing the SIS may be used to temporarily adhere the device 10 to the walls of the body vessel. If the device 10 is only deployed within the body vessel temporarily, host cells of the walls may adhere to the device, but will not differentiate, allowing for later retrieval of a device 10 from the body vessel.

FIGS. 4a-5b depicts a body vessel embolization kit 30 which implements the occluding device 10 in accordance with one embodiment of the present invention. As shown, the kit 30 includes a microcatheter 32 defining a catheter lumen and is preferably made of a soft, flexible material such as silicone or any other suitable material. Generally, the microcatheter 32 has a proximal end 34, a distal end 36, and a plastic adapter or hub 38 to receive an apparatus to be advanced therethrough. In one example, the inside diameter of the microcatheter 32 may range between 0.014 and 0.027 inches. The kit 30 may further include a guide wire 40 which provides the guide catheter 42 a path during insertion of the guide catheter 42 within a body vessel 44. The size of the guide wire 40 is based on the inside diameter of the guide catheter 42.

In one embodiment, the guide catheter 42 is a polytetrafluoroethylene (PTFE) guide catheter or sheath for percutaneously introducing the microcatheter 32 into a body vessel 44. Of course, any suitable material may be used without falling beyond the scope or spirit of the present invention. The guide catheter 42 may have a size of about 4-French to 8-French and allows the microcatheter 32 to be inserted therethrough to a desired location in the body vessel 44. The guide catheter 42 receives the microcatheter 32 and provides stability of the microcatheter 32 at a desired location of the body vessel 44. For example, the guide catheter 42 may stay stationary within a common visceral artery, e.g., a common hepatic artery, adding stability to the microcatheter 32 as the microcatheter 32 is advanced through the guide catheter 42 to a point of occlusion in a connecting artery, e.g., the left or right hepatic artery.

When the distal end 36 of a microcatheter 32 is at a point of occlusion in the body vessel 44, the occluding device 10 may be loaded at the proximal end 34 of the microcatheter 32. The stylet wire 18 may then be retracted from the lumen 16 of the coil 12 where the coil 12 is then restrained from curling by the microcatheter 32, e.g. by the lumen of the microcatheter 32. In one example, the occluding device 10 may be "pre-package" within a loading cannula (not shown) and butted up against hub 38 for delivery into the microcatheter 32. In this scenario, the microcatheter 32 may be provided with the occluding device 10 having the stylet wire 18 either present or already removed.

The occluding device 10 is advanced through the microcatheter 32 for deployment through the distal end 36. A push wire 126 may be used to mechanically advance or push the occluding device 10 through the microcatheter 32. The size of the push wire 126 depends on the diameter of the microcatheter 32.

It is to be understood that the body vessel embolization kit 30 described above is merely one example of a kit 30 that may be used to deploy the occluding device 10 into a body vessel 44. Of course, other kits, assemblies, and systems may be used to deploy any embodiment of the occluding device 10 without falling beyond the scope or spirit of the present invention.

Figure 5A:
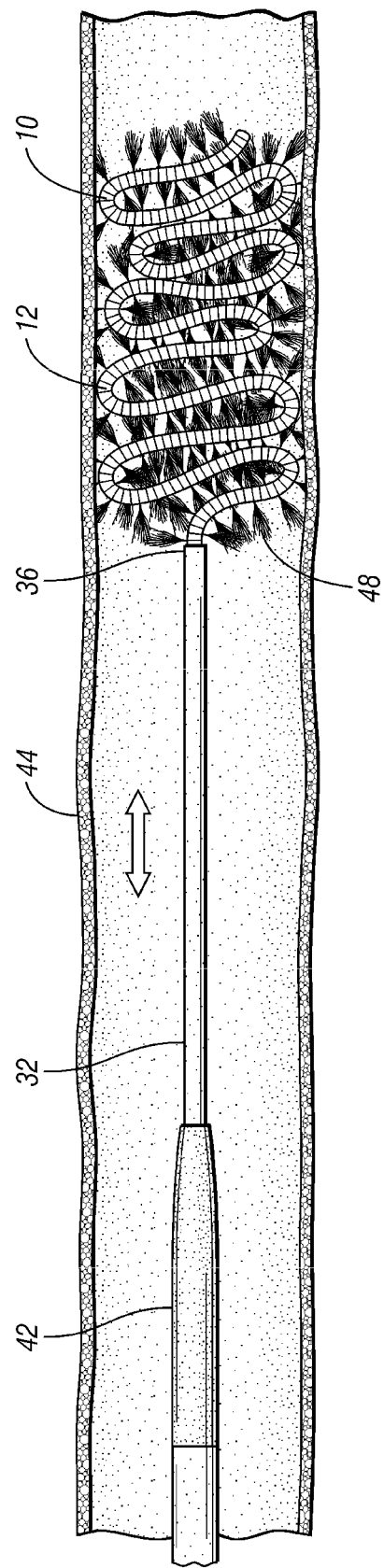
FIG. 5a is a partial side view of the embolization kit with a deployed occluding device in accordance with an embodiment of the present invention.
Figure 5B:
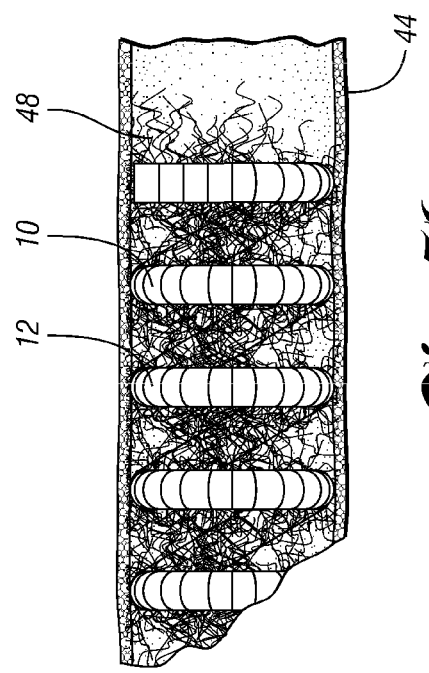
FIG. 5b is a partial side view of a deployed occluding device in accordance with another embodiment of the present invention.

FIGS. 5a and 5b further illustrate two examples of a curled coil 12 within the lumen of the body vessel 44. FIG. 5a illustrates the curled coil 12 having a looping and folding configuration. FIG. 5b illustrates the curled coil 12 having a helical configuration. Other curled configurations for the coil 12 that are suitable for occluding a body vessel 44 are also intended to be within the scope and spirit of the present invention. Moreover, the coil 12 may also include fibers 48 extending therefrom, which preferably facilitate occlusion of the body vessel 44. The fibers may or may not have the coating 20 attached thereto.

Applicants performed the following two studies which illustrate the affect of restraining a coated, pre-curled tensioned coil from curling until being deployed in accordance with at least one embodiment of the present invention. In the first study, non-tensioned coils having an extended embolus diameter and length of about 0.035 inches and 5 centimeters, respectively, were coated in a straightened configuration by being dipped 2 times in a low concentration of SIS solution followed by 6 dips in a high concentration SIS solution. The low concentration of SIS solution contained 1 ml of SIS gel and 3 ml of Phosphate Buffered Saline (PBS) and the high concentration of SIS solution contained 1 ml of SIS gel and 1 ml of PBS. Between each of the dipping steps, the coils were dried by being hung in a vacuum oven at 37 degrees Celsius (C.) for two hours followed by air-drying in a laminar flow hood for 15 minutes. The drying steps caused the SIS gel to polymerize via crosslinking to form a solid coating layer around each of the coils. The coated coils were then pushed over a "kinked" stylet wire to pre-curl tension the coils for curling to a coiled embolus diameter and configuration of about 5 millimeters and 3.1 loops respectively. However, pre-tensioning and curling of the coated coils resulted in delamination of nearly 100% of the SIS solid coating layer from the coils. Accordingly, deployment testing for evaluating coating loss during deployment was not conducted due to the extreme pre-deployment coating losses.

In the second study, pre-curled tensioned coils having an extended embolus diameter and length of about 0.035 inches and 5 centimeters, respectively, and a coiled embolus diameter and configuration of about 5 millimeters and 3.1 loops, respectively, were coated by the same dipping and drying process of the first study including using equivalent SIS solution concentrations for the dipping steps. However, the pre-curled tensioned coils were restrained in a straight configuration during coating and up until being deployed by having a substantially straight stylet wire positioned through each of the corresponding coil lumens. On average, the coils were each coated with a total of 4.10 mg of SIS gel post-polymerization to provide about 45.9 microns of SIS coating thickness around the coils. The coils were then separately loaded into corresponding catheters, which had been flushed with saline, and deployed from their respective catheters. After deployment, the loss of any coating from each of the coils was determined. On average, the coils lost 23.2% of the SIS coating. Notably, however, about 76.8% of the SIS coating still remained on the coils after deployment from the second study, whereas essentially no coating remained on the coils from the first study even before they were deployed. Accordingly, Applicants found that by restraining the coated, pre-curled tensioned coil substantially straight until being deployed that cracking and/or chipping of the coating prior to introduction of the coil into the body vessel may be reduced to preferably enhance occluding performance of the coil.

As a person skilled in the art will readily appreciate, the above description is meant as an illustration of the implementation of the principles of this invention. This description is not intended to limit the scope or application of this invention in that the invention is susceptible to modification, variation, and change, without departing from the spirit of this invention, as defined in the following claims.

The invention claimed is:

1. A method for making an occluding device for occlusion of fluid flow through a lumen of a body vessel, the method comprising:

attaching a coating to an embolization coil that is substantially straight, the coating being nominally strained thereon and the embolization coil having a pre-curled tension to facilitate the embolization coil to be curled within the lumen of the body vessel when deployed; and constantly restraining the embolization coil from curling during and after attaching the coating until delivering the coil within the body vessel to reduce pre-deployment straining of the coating including containing a stylet wire within the embolization coil, the stylet wire being substantially straight to restrain the embolization coil from curling.

2. The method according to claim 1 wherein the coating comprises small intestinal submucosa (SIS).

3. The method according to claim 1 wherein the embolization coil has a lumen formed therethrough and the step of containing the stylet wire includes containing the stylet wire within the lumen of the embolization coil.

4. The method according to claim 3 further comprising advancing the stylet wire through the lumen of the embolization coil to straighten the embolization coil prior to the step of attaching the coating.

5. The method according to claim 3 wherein the step of restraining the embolization coil further includes introducing the embolization coil into a microcatheter subsequent to the step of attaching the coating, the microcatheter being configured to restrain the embolization coil from curling and to deploy the embolization coil.

6. The method according to claim 5 wherein the step of restraining the embolization coil further includes removing the stylet wire from the lumen of the embolization coil, the embolization coil being restrained from curling via the microcatheter.

7. The method according to claim 1 wherein the step of attaching the coating includes coating the embolization coil with small intestinal submucosa (SIS) gel comprising SIS and water, and drying the SIS gel to form the coating.

* * * * *